Aug. 10, 1971 R. W. HYDE Plant Pat. 3,055
ROSE PLANT
Filed Aug. 19, 1969
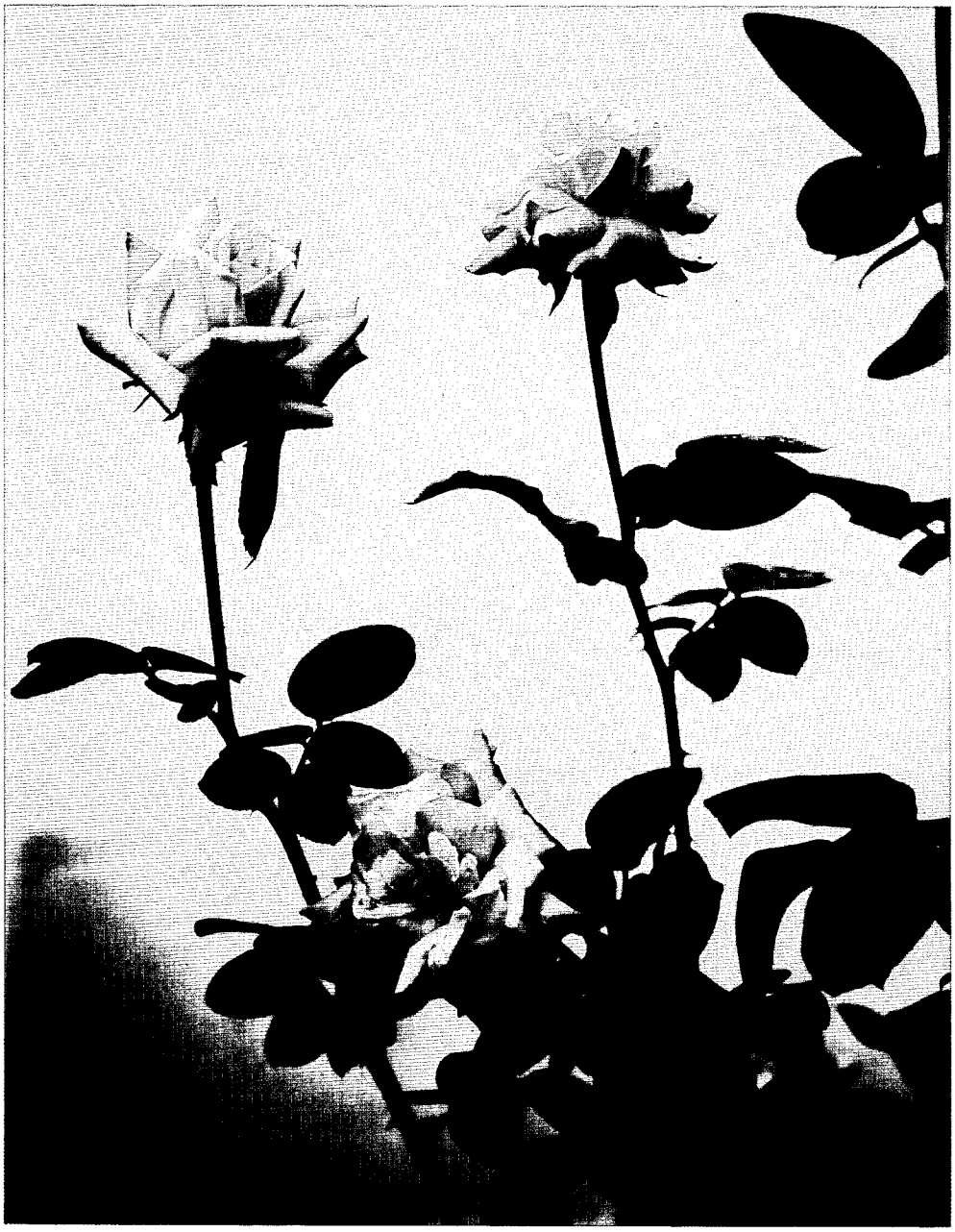
Inventor
Robert W. Hyde
By: Robb & Robb
Attorneys United States Patent Office Plant Pat. 3,055
Patented Aug. 10, 1971

3,055

ROSE PLANT

Robert W. Hyde, 1 Putter Place,
Crystal River, Fla. 32629

Filed Aug. 19, 1969, Ser. No. 851,502
Int. Cl. A01h *5/00*
U.S. Cl. Plt.—11 1 Claim The present invention relates to a new and distinct variety of rose plant of the hybrid tea class, which was discovered by me as a cultivated but sport of the rose variety known as "Swarthmore" (Plant Patent No. 2,444), said discovery having been made on my cultivated property located at Crystal River, Fla.

At the time of my discovery, I was growing a small block of plants of the parent variety "Swarthmore" among an outdoor group planting of several hundred rose plants of various varieties. During my care of these plants, my attention was attracted to one particular plant of the "Swarthmore" variety which bore some blooms of a color distinctly different from the color of the other blooms on the same plant, and different from the normal bloom color of the other plants of the "Swarthmore" variety. Upon closer inspection of this plant, I found that it has sported, and I thereupon took immediate steps to preserve the sport and keep it under close observation. Continued observations of the original sport and progeny thereof produced by me, at Crystal River, Fla., by grafting and also by rooting leafy cuttings conclusively established that the sport is definitely distinguished from its parent, as well as from all other rose varieties of which I am aware, as evidenced by being substantially identical to the parent variety except for its different flower color which is basically light pink in color, with bright and lighter or darker pink edges, combined with a stronger flower fragrance. These distinguishing characteristics are fixed and transmissible through succeeding propagations.

In the case of the parent variety "Swarthmore," the flower edges tend to darken or blacken, particularly in the spring and fall blooms, which detracts from the attractiveness of the flowers and constitutes a definite drawback to public acceptance from a commercial standpoint.

While the flowers of my new sport closely resemble those of the rose variety known as "Anne Letts" (unpatented) in respect to their shape and basic color, the flowers of "Anne Letts" are more uniform and substantially the same color throughout without any change in the edge color.

The accompanying drawing shows typical specimens of the vegetative growth and flowers of my new rose variety in different stages of development and as depicted in color as nearly true as it is reasonably possible to make the same in a color illustration of this character.

Being substantially identical to the parent variety, except for the aforementioned distinctions, it is unnecessary to specifically describe the new sport in complete detail and it may be considered as otherwise conforming to the detailed description embodied in Plant Patent No. 2,444, issued Sept. 8, 1964, to which reference may be readily had. However, for convenience, the following description of the flower colors of the new sport is given, with color terminology being in accordance with Ridgway's Color Standards and Nomenclature, except where general color terms of ordinary dictionary significance are obvious:

Buds:

*Color.*—Cameo Pink, Plate XII, with edges of Thulite Pink, Plate XII, blending through Pale Rosolane Purple, Plate XXVI to the main Cameo Pink color.

Half-open flowers:

*Color.*—Thulite Pink, Plate XII, edged with Spinel Red, Plate XXVI at outer edges.

Fully open flowers:

*Color.*—From Rosolane Pink, Plate XII to Rose Pink, Plate XII, with outer edges of petals varying from Spinel Red, Plate XXVI to Pomegranate Purple, Plate XII; in strong summer sunlight, the open flowers fade slightly lighter to Rose Pink, Plate XII, and the bright outer edges of the petals also fade back to Tyrian Pink, Plate XII, but have a slightly stronger intensity (chroma) than the plate colors aforesaid.

In partial shade, the entire flowers are about one shade lighter as follows:

Buds:

*Color.*—Cameo Pink, Plate XII, edged with Rosolane Pink, Plate XII.

Half-open flowers:

*Color.*—Rosolane Pink, Plate XII, edged with Thulite Pink, Plate XII.

Fully open flowers:

*Color.*—Cameo Pink, Plate XII, edged with Rosolane Purple, Plate XXVI.

I claim:

1. A new and distinct variety of rose plant of the hybrid tea class, substantially as herein shown and described, characterized particularly as to novelty by being substantially identical with the variety known as "Swarthmore" (Plant Patent No. 2,444) except for its flower color and fragrance, said flower color being basically light pink, with bright and lighter or darker pink petal edges, and said flowers having a stronger fragrance than those of "Swarthmore."

No references cited.

ROBERT E. BAGWILL, Primary Examiner